(12) United States Patent
Krammer

(10) Patent No.: US 9,057,637 B2
(45) Date of Patent: Jun. 16, 2015

(54) METHOD AND DEVICE FOR THE OPTICAL MEASUREMENT OF STATE VARIABLES AND THE LEVEL IN A CONTAINER FOR LIQUEFIED GASES, AND DEVICE THEREFOR

(75) Inventor: Gert Krammer, Graz (AT)

(73) Assignee: Magna Steyr Fahrzeugtechnik AG & Co. KG, Graz (AT)

( * ) Notice: Subject to any disclaimer, the term of this patent is extended or adjusted under 35 U.S.C. 154(b) by 1535 days.

(21) Appl. No.: 12/445,865

(22) PCT Filed: Oct. 16, 2007

(86) PCT No.: PCT/EP2007/008963
§ 371 (c)(1),
(2), (4) Date: Jun. 1, 2010

(87) PCT Pub. No.: WO2008/046585
PCT Pub. Date: Apr. 24, 2008

(65) Prior Publication Data
US 2010/0281972 A1    Nov. 11, 2010

(30) Foreign Application Priority Data
Oct. 17, 2006 (AT) ............... GM 751/2006

(51) Int. Cl.
| | | |
|---|---|---|
| *G01J 1/04* | (2006.01) | |
| *G01N 15/06* | (2006.01) | |
| *G01F 23/292* | (2006.01) | |
| *G01D 5/353* | (2006.01) | |
| *G01N 21/00* | (2006.01) | |
| *G01N 21/41* | (2006.01) | |

(52) U.S. Cl.
CPC .......... *G01F 23/292* (2013.01); *G01D 5/35303* (2013.01); *G01N 21/00* (2013.01); *G01N 21/4133* (2013.01); *G01N 2201/0846* (2013.01)

(58) Field of Classification Search
CPC .......... G01N 21/3504; G01N 21/3554; G01N 21/3577; G01N 21/3581; G01N 21/359; G01N 21/41; G01N 21/47; G01J 3/42; G01F 23/28; G01F 23/282; G01F 23/284; G01F 23/292; G01F 23/2921; G01F 23/2922; G01F 23/2924; G01F 23/2925; G01F 23/29
USPC ............ 385/12; 250/900, 904–908, 573–577, 250/564, 565, 227.24, 227.25, 227.14, 250/559.04, 559.05, 227.11; 356/437–442, 356/246; 73/64.41, 290 R, 293, 291, 292, 73/19.01, 19.1, 19.11, 23.2
See application file for complete search history.

(56) References Cited

U.S. PATENT DOCUMENTS 4,837,777 A * 6/1989 Jones et al. .................. 374/142
4,936,681 A   6/1990 Ruhrmann
(Continued)

FOREIGN PATENT DOCUMENTS

DE    19959279    6/2001
(Continued)

*Primary Examiner* — Pascal M Bui Pho
(74) *Attorney, Agent, or Firm* — Bachman & LaPointe, P.C.

(57) ABSTRACT

A method and a device for optically determining state variables inside a container (1) for liquefied gases. In the method and device, light emitted by an illumination unit (2) travels within an optical waveguide (7, 9) to a contact point (33) with the content of the container (1) and is partially reflected there, the intensity of the reflected light is measured by an image sensor (4), and a state variable is determined from the intensity. In order to create a comprehensive "image" of the state variables in the container and of the container content, several optical waveguides (29, 29') are guided to contact points (33) which are distributed within the container (1) and form measurement points (9.1, 9.2, 9.3, . . . , 9.n). Locally assigned state variables (refractive index, density, temperature, etc.) of the container content are determined from the measured values obtained at the measurement points (9.1, 9.2, 9.3, . . . , 9.n) and are evaluated along with the spatial coordinates of the measurement points (9.1, 9.2, 9.3, . . . , 9.n) in the container (1).

5 Claims, 2 Drawing Sheets

(56) References Cited

U.S. PATENT DOCUMENTS

| | | | |
|---|---|---|---|
| 7,710,567 B1 * | 5/2010 | Mentzer et al. | 356/436 |
| 2004/0021100 A1 * | 2/2004 | Gouzman et al. | 250/573 |
| 2006/0066859 A1 | 3/2006 | Downey | |

FOREIGN PATENT DOCUMENTS

| | | |
|---|---|---|
| EP | 0176194 | 4/1986 |
| FR | 2552544 | 3/1985 |
| WO | 88/01738 | 3/1988 |

* cited by examiner

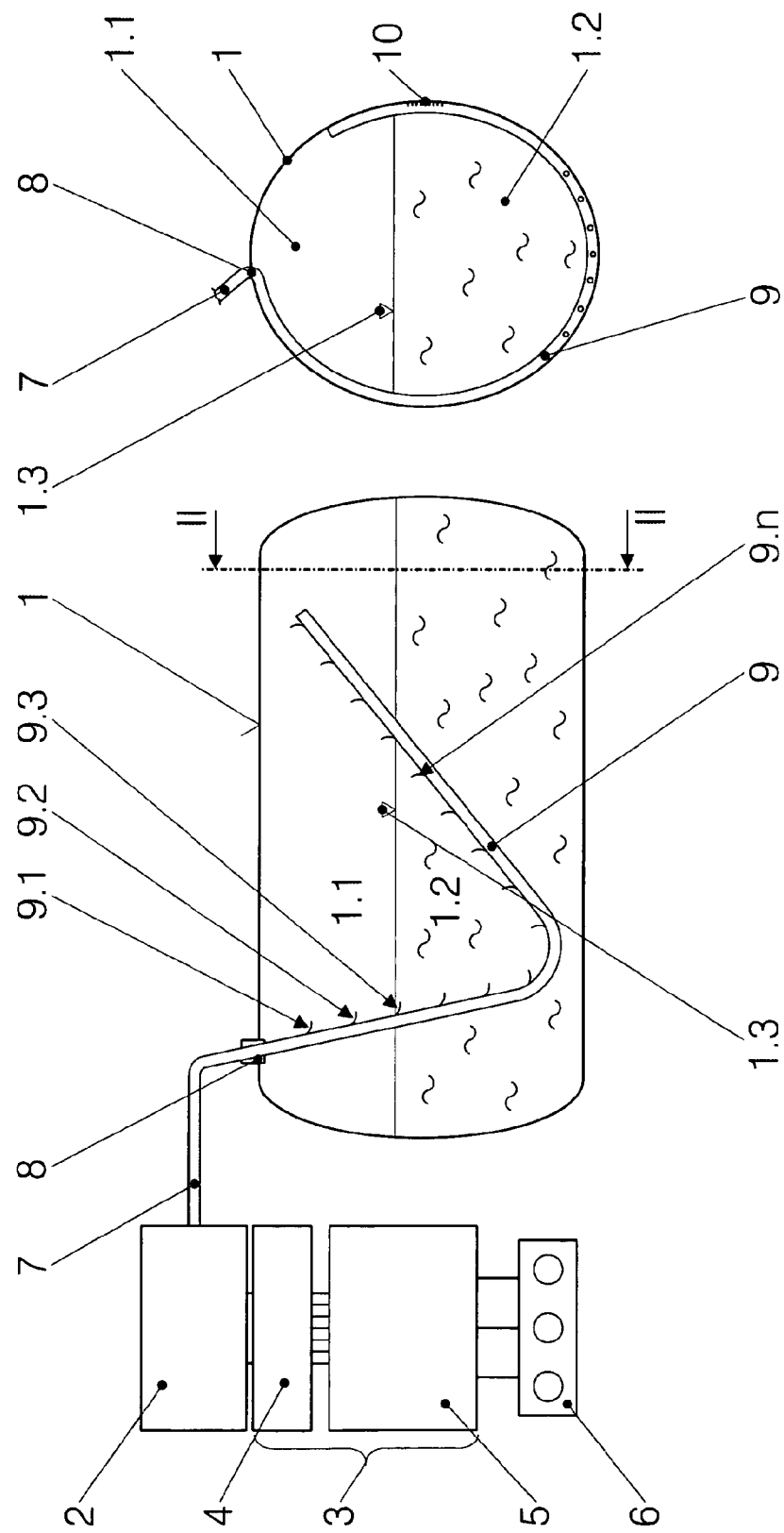

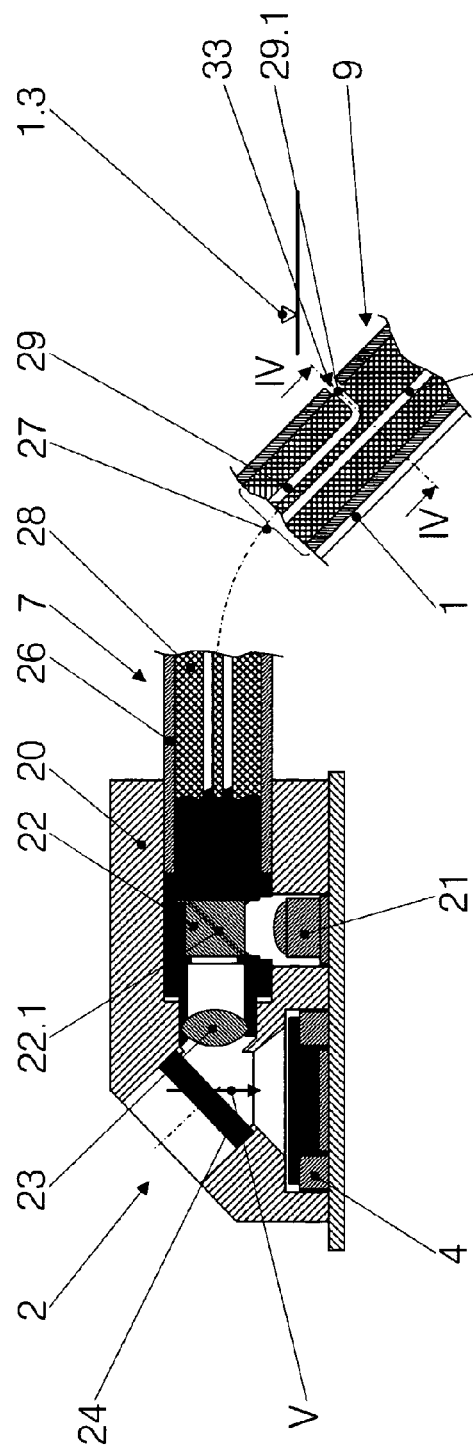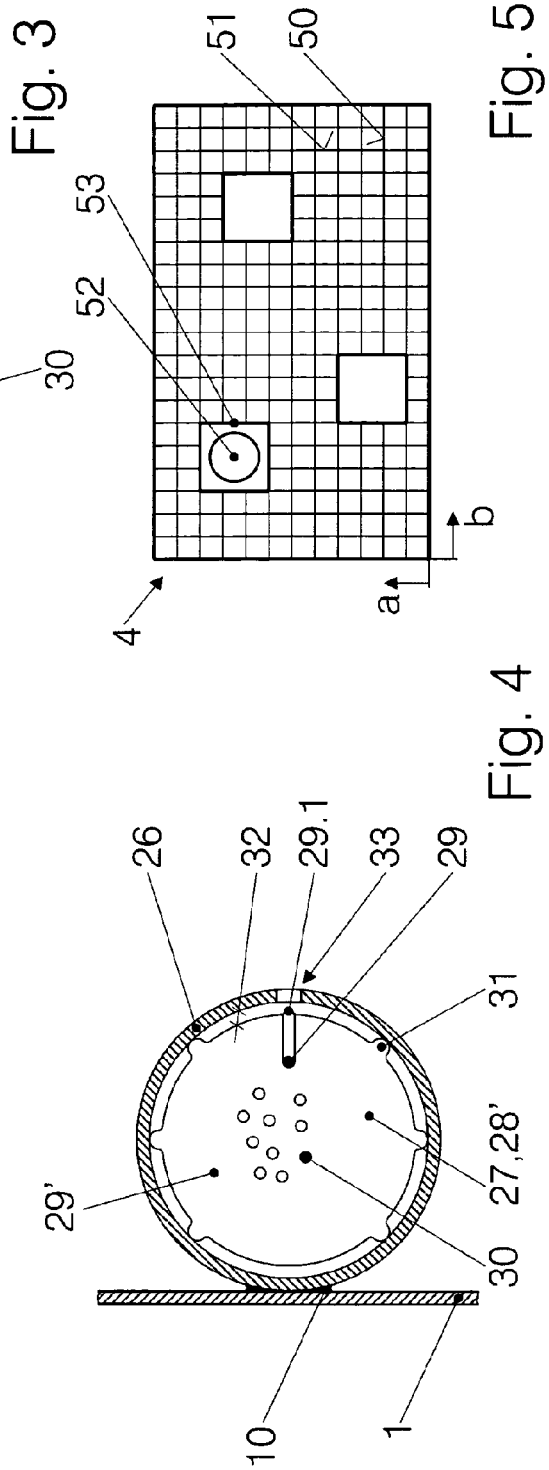

METHOD AND DEVICE FOR THE OPTICAL
MEASUREMENT OF STATE VARIABLES AND
THE LEVEL IN A CONTAINER FOR
LIQUEFIED GASES, AND DEVICE
THEREFOR

BACKGROUND OF THE INVENTION

The invention relates to a method for the optical determination of state variables in the interior of a container for liquidified gases, where light which is emitted from a lighting unit is carried in an optical waveguide to a contact point with the content of the container, where it is partially reflected and the light intensity of the reflected light is measured, and a state variable is determined from this and from the light intensity of the light emerging from the light source.

The container is intended to be a container for low-boiling-point gases—in particular hydrogen—which is carried by a motor vehicle, with the gases being used as fuel. Liquefied low-boiling-point gases are stored in conditions (pressure and temperature) in which the state variables of the liquid phase and of the gaseous phase differ only slightly. Furthermore, the physical and thermal characteristics, in particular of hydrogen, and the heat which is invariably introduced into the interior of the container even with the best insulation leads to an inhomogeneous temperature distribution and mass density distribution in the container.

For safety reasons and in order to make use of the range of one container filling, accurate monitoring of state variables and, furthermore, accurate determination of the amount of fuel still available are required for use in a motor vehicle. The expression state variables means not only the mass density, pressure and temperature but also the phase state (liquid or gaseous). Furthermore, there are certain exacerbating factors which are typical for driving operation, for example the fact that the position of the liquid level is influenced by the inclination of the vehicle and by centrifugal forces.

Conventional level measurement systems have either not satisfied the requirements or have been found to be much too expensive and also unreliable. Electrical measurement methods (capacitive, inductive) require the introduction of electrical lines into the (double-walled) container, which results in heat bridges and a risk of explosion, and, furthermore, they are susceptible to defects and are sensitive to disturbances. Mechanical systems with moving parts are completely impracticable in the low-temperature range.

DE 199 59 279 A1 discloses a method and a device for the optical level measurement in a cryostatic container, in which an optical waveguide touches the container content by means of a sensor surface which is extended in its longitudinal direction. Scattering losses occur in consequence as a function of the refractive index of the container content touching the sensor surface, and these losses increase in proportion to the sensor area and thus to the container content. This allows the liquid level height to be measured. However, because of the poor dependency of the liquid level on the scattering losses and because of the cumulative evaluation of all the scattering losses for the determination of the position of the liquid level, this is not sufficiently accurate. Furthermore, the amount of fuel in the form of gas above the liquid level must also be taken into account for particularly accurate measurement of the available amount of fuel.

SUMMARY OF THE INVENTION

An object of the invention is to provide a method which overcomes the above problems and provides a comprehensive "image" of the state variables in the container as a basis for vehicle operation. In this case "image" is meant in the transcribing sense: states which are associated with individual points in the container and can be connected to form locus curves of identical states. A further object is to provide a device for carrying out the method, which is simple and functionally reliable even in the severe conditions in a motor vehicle.

The method according to the invention consists in that a plurality of optical waveguides are passed to measurement points which are distributed in the interior of the container and state variable, which can be associated locally, are determined from the measured values obtained therein, and these state variables are evaluated together with the spatial coordinates of the measurement points, thus resulting in a spatial "image" of the state variables. Since the optical waveguides are not in contact with the container content over an extended area, but only at individual precisely defined measurement points, they provide accurate measured values at defined points.

The measured values are first of all reflected amounts of light, which can be converted directly to a refractive index. Amounts of light and the refractive index calculated from them can be converted to state variables or can be compared directly with a threshold value in order to decide whether the measured value corresponds to the liquid phase state or gaseous phase state. The state variable is then either one or the other phase state.

For example, the measured values can be compared with a table in order to decide whether the state variable is "liquid" or "gaseous" for each measurement point there. In the simplest case, the table contains a limit value which is determined by a simple experiment, above or below which one or the other phase state exists. In consequence, the position of the liquid level is determined from the position of the measurement points at which the state is "liquid" and the filling volume of liquid in the container is determined from this, using the dimensions of the container, and, furthermore, the filling mass is determined by means of the substance values.

In a theoretically based and therefore preferred method, either the refractive indices are determined first of all, from the difference between the light intensities (before and after passing through the optical waveguide) and the densities are determined at the individual measurement points from the refractive indices, or the densities are determined directly on the basis of a second table.

A refinement of the method consists in that total filling mass in the container (gaseous and liquid) is determined from the density at all the measurement points (also in those where the container content is gaseous) and from the dimensions of the container, by calculating partial volumes corresponding to the measurement points, and these partial masses are calculated using the mass density which is measured in the respective measurement point and these are added.

One valuable development of the method consists in that the temperature distribution in the container is determined from the density at all measurement points and from the pressure in the container. Because of the thermal characteristics of cryogenic gases, the temperature distribution in the container is inhomogeneous. The invention for the first time makes it possible to measure inhomogeneities such as these—which may be safety-relevant.

In one particularly simple process, although this is less accurate, the amount of liquid in the container is determined from the mean value of the measured values at all the measurement points and from the dimensions of the container.

Furthermore, the invention consists in a device for the optical measurement of the state variables in a container for liquidified gases, which comprises a lighting unit, an optical waveguide unit and an evaluation unit.

According to the invention, a bundle of optical waveguides is guided into the container, the outer ends of which are optically connected via a beam splitter to the light source, and whose inner ends are arranged at measurement points which are distributed in the area of the container and are in contact with the contact of the container, and the beam splitter is furthermore optically connected to the evaluation unit, which evaluation unit comprises an image sensor and a computer, wherein the image sensor measures the light intensities reflected in the individual optical waveguides and makes the measured value available to the computer, and wherein the computer determines state variables in the container therefrom and from the position coordinates of the measurement points.

Since only the end surface at the inner end of the optical waveguide is in contact with the surrounding medium, the difference, caused by partial reflection, between the light intensities before and after passing through the optical waveguide is greater and can therefore be measured more accurately than with an optical waveguide whose outer surface touches the surrounding medium and which emits limits thereto only by scattering. Furthermore, according to the invention, a measurement is taken only at a defined point. This is the only way in which it is possible to detect not only the phase state but also state variables in the relatively narrow sense, such as mass density and temperature, with good accuracy. The multiplicity of measurement points which are distributed in the area of the container and whose position is known results in a three-dimensional "image" of the state variables, at least along the optical waveguide bundle which is routed or laid in a suitable manner in the area of the container, in which case the word "image" should be understood in the wider sense.

The light source, the beam splitter and the evaluation units are preferably fitted outside the container, and the bundle of optical waveguides which originates from the beam splitter is passed through the walls of the container into its interior. A single entrance opening into the (double-walled) container is therefore sufficient for the entire bundle of optical waveguides, and this bundle requires only one common beam splitter. Finally, there is no need to pass any electrical lines into the container, and the bundle can be prefabricated together with the light source and beam splitter before being fitted in the container.

In this case, the bundle of optical waveguides forms a strand, which comprises a matrix and a number (which may be very large) of optical waveguides embedded therein, with each optical waveguide being passed to a different point with respect to the surface of the strand, and with the points being distributed over the length of the strand. The end of one optical waveguide is in contact with the content of the container at each point. The ends of the optical waveguides in the container have an end surface which is at right angles to their longitudinal axis, and this end surface is in contact with the content of the container. In other words, the optical waveguides in the strand have different lengths, and their end surfaces project at points which are distributed over the outer surface of the strand. One refinement consists in that the bundle contains one or more reference fibers which follow the bundle as far as the end or as far as particular points in order then to return to the beam splitter, without touching the container content. An additional fiber such as this is used as a reference for the light intensity injected from the light source and as a monitor, signaling that the strand has been damaged or broken. The complete strand can be prefabricated by means of a suitable device, outside the container.

There are various options for delaying and routing of the strand in the container, routing it such that it passes a plurality of spatial points. To this end, it is advantageous for the strand which forms the bundle to be surrounded by an envelope tube, best of all at a short radial distance, which envelope tube forms a vessel which communicates with the content of the container. The envelope tube is therefore used not only to guide and support the strand, but in fact damps rapid changes in the liquid level, which occur during use in a vehicle.

In one preferred embodiment, the envelope tube is curved, and the strand which forms the bundle is flexible, and is preferably spatially curved and is attached to the inner wall of the container. Measurement points can thus be arranged at all the major points, using a single envelope tube and a single strand guided therein. The envelope tube is permanently installed at the same time that the container is constructed, and the flexible strand can be inserted into the envelope tube later, from the outside. This means that the strand can also easily be replaced. If the envelope is in the form of a helical line, it can be attached to the inner wall of the container (for example by welding) over its entire length, and can be provided with holes distributed over the length. The former provides protection against sensitivity to oscillations, and the holes ensure communication between the container content and the space between the strand and the envelope tube, for all filling levels.

A single image sensor such as the type normally used in video cameras is advantageously used for measurement of the amount of light returning from the optical waveguides via the common beam splitter. One cheap mass-produced item is therefore used instead of a multiplicity of individual sensors. The planar arrangement of a×b pixels is utilized particularly well if each optical conductor has an associated field of a plurality of pixels, of 4 to 25 pixels, preferably 9. The light which is reflected in the respective optical waveguide is thus imaged onto a field such as this with a side length of 3 to 5 pixels. This makes it possible to compensate for position tolerances and the failure of one pixel.

The evaluation of the measured value is considerably simplified if the association between the position of the pixels on the image sensor onto which the outer end of the optical waveguide is mapped and the position of the inner end of the optical waveguide in the container is stored in the evaluation unit for each optical waveguide.

BRIEF DESCRIPTION OF THE DRAWINGS

The invention will be described and explained in the following text with reference to figures, in which:

FIG. 1: shows a schematic longitudinal section through a container having a device according to the invention, FIG. 2: shows a section along II-II in FIG. 1

FIG. 3: shows the device according to the invention from FIG. 1 in detail,

FIG. 4: shows a section along IV-IVI in FIG. 3,

FIG. 5: shows a plan view in the direction V in FIG. 3.

DETAILED DESCRIPTION

FIG. 1 indicates a container for liquefied cryogenic gases only by means of its wall 1. Physical containers are generally double-walled with a highly insulating space between them. The cryogenic gas in its interior forms a gaseous phase 1.1 and a liquid phase 1.2, which is separated from the gaseous phase 1.1 by a liquid level 1.3. A device which comprises a lighting unit 2 and an evaluation unit 3, outside the container, is provided in order to determine state variables of the container content. The evaluation unit 3 comprises an image sensor 4, a computer 5 and an indication of the determined state variables or amount contained 6. Furthermore, the device comprises an optical waveguide unit, which originates from the lighting unit 2 and comprises an outer part 7 and an inner optical waveguide unit, the inner part 9, which is passed through a bushing 8 into the interior of the container 1. As described in more detail further below, the optical waveguide unit 7, 9 contains a number of individual optical waveguides, in this case glass fibers, which are in contact with the content of the container at various points 9.1, 9.2, 9.3, . . . 9.n in the inner part 9 of the optical waveguide unit.

The inner part 9 of the optical waveguide unit can pass through the container 1 in a straight line at an inclined angle. In the illustrated exemplary embodiment, it runs in the form of a spiral (in particular a helical line) along the inner wall 1 of the container, which is approximately cylindrical in this case, see also FIG. 2. This results in measurement points distributed over the entire internal contour of the container, using a single optical waveguide unit.

FIG. 3 shows the lighting unit 2 and a part of the inner optical waveguide unit 9 in more detail. In a housing 20, the lighting unit 2 contains a light source 21, a beam splitter 22, a lens 23 and a mirror 24. The light emitted from the light source 21 is deflected on the reflection surface 22.1 of the beam splitter 22 to the optical waveguide unit 7. This comprises an envelope tube 26, which is or can be permanently connected to the housing 20, and a number of optical waveguides 29 in it, only one of which optical waveguides 29 is shown (although there may be a very large number of them) and which optical waveguides 29 are incorporated in a matrix 28. The light which is emitted from the light source 21 is thus passed into the optical waveguide 29, distributed uniformly.

In the inner part 9 of the optical waveguide unit, the optical waveguide 29 is bent at right angles at a specific point, as a result of which it leaves the matrix 28 and its end surface 29.1 is in contact with the container content through the hole 33 in the envelope tube 26. A portion of the light is scattered into the container content at the surface 29.1 and a portion is reflected, as a result of which it is passed back again to the beam splitter 22 in the same optical waveguide. The light which is passed back is not stopped by the reflection surface 22.1 of the beam splitter 22, and is passed via the lens 23 and the mirror 24 to the image sensor 4.

FIG. 4 shows the inner part 9 of the optical waveguide unit, in the form of a cross section. As can be seen, the metallic envelope tube 26 is welded to the wall 1 of the container, as a result of which it cannot oscillate in response to vibration from the vehicle. The strand 27 is located in the interior of the envelope tube 26 and is formed by a matrix composed of flexible plastic in which the optical waveguide 29 and a large number of further optical waveguides 29', which are only indicated, as well as a reference conductor 30 are incorporated. The optical waveguide 29 is passed outwards to the outer surface of the strand 27, at the location of the hole 33. The strand itself is at a distance 32 from the inner wall of the envelope tube 26, and is supported here by means of studs 31 in the envelope tube 26. In this way, the container content can be connected to and communicate with the container content through the hole 33 and the large number of other holes, which are each associated with one measurement point 9.1, 9.2 etc. The studs 31 make it easier to insert the strand 27 into the curved envelope tube, which can thus be installed and replaced from the outside.

FIG. 5 shows a plan view of the image sensor 4, which is a commercially available, mass-produced item, of known design. This schematic illustration shows horizontal and vertical grid lines 50, 51 which form squares, each of which corresponds to one pixel. The circle 52 shows the image of the light reflected from the optical waveguide 29 on the image sensor 4. As can be seen, this is associated with a field 53, which in this case comprises 3×3, that is to say 9, pixels. Since a plurality of pixels are associated with the circle 52, it is possible to compensate for position tolerances and the failure of one pixel, thus achieving better measurement accuracy and reliability overall.

The invention claimed is:

1. A method for the optical determination of state variables in the interior of a container for liquidified gases, where light which is emitted from a lighting unit is carried in an optical waveguide to a contact point with the content of the container, where it is partially reflected and the light intensity of the reflected light is measured, and a state variable is determined from the measured reflected light and from the light intensity of the light emerging from the light source, a plurality of optical waveguides are passed to contact points which form measurement points which are distributed in the interior of the container and state variable, which can be associated locally, of the container content are determined from the measured values obtained therein, and these state variables are evaluated together with the spatial coordinates of the measurement points in the container, thus resulting in a spatial image of the state variables, and determining local refractive index of the container content at the measurement points from the measured light intensity, and each measurement point is used to decide whether the state variable is liquid or gaseous at the measurement points, first calculating the refractive indices from the measured values of the reflected light intensity at the measurement points, and thereafter calculating the density from the refractive indices as a state variable at the respective measurement point, wherein total filling mass, both liquid content and gaseous content in the container is determined from the density at all the measurement points and from the dimensions of the container, by calculating partial masses from the mass densities measured at the respective measurement point for partial volumes which are defined corresponding to the measurement points, including both the liquid and gaseous content, and these partial masses are added.

2. The method as claimed in claim 1, wherein the position of the liquid level is determined from the spatial coordinates of the measurement points at which the state is liquid and the filling volume of liquid in the container is determined, using the dimensions of the container, and, furthermore, the filling mass is determined by means of the measured values.

3. The method as claimed in claim 1, wherein the relationship between each refractive index and a density is taken from a table.

4. The method as claimed in claim 3, wherein the temperature distribution in the container is determined from a density at all measurement points and from the pressure in the container.

5. The method as claimed in claim 1, wherein the amount of liquid in the container is determined from the mean value of the measured values at all the measurement points and from the dimensions of the container.

\* \* \* \* \*